US008306292B2

(12) United States Patent
Moriya

(10) Patent No.: US 8,306,292 B2
(45) Date of Patent: Nov. 6, 2012

(54) IMAGE DISPLAY DEVICE AND IMAGE DISPLAY PROGRAM STORAGE MEDIUM

(75) Inventor: Yoshiyuki Moriya, Tokyo (JP)

(73) Assignee: Fujifilm Corporation, Tokyo (JP)

( * ) Notice: Subject to any disclaimer, the term of this patent is extended or adjusted under 35 U.S.C. 154(b) by 896 days.

(21) Appl. No.: 12/210,278

(22) Filed: Sep. 15, 2008

(65) Prior Publication Data

US 2009/0087047 A1 Apr. 2, 2009

(30) Foreign Application Priority Data

Sep. 28, 2007 (JP) ................................ 2007-256292

(51) Int. Cl.
*G06K 9/00* (2006.01)
*G06K 9/34* (2006.01)
(52) U.S. Cl. ......... 382/128; 382/131; 382/173; 382/132
(58) Field of Classification Search .................. 382/128, 382/131, 298, 130, 129, 132, 173, 219, 220, 382/282
See application file for complete search history.

(56) References Cited

U.S. PATENT DOCUMENTS

| 5,982,953 A | 11/1999 | Yanagita et al. | |
|---|---|---|---|
| 2004/0081342 A1* | 4/2004 | Sato | 382/128 |
| 2005/0105828 A1* | 5/2005 | Oosawa | 382/294 |
| 2006/0181551 A1* | 8/2006 | Matsumoto | 345/679 |

FOREIGN PATENT DOCUMENTS

| JP | 8-76741 A | 3/1996 |
|---|---|---|
| JP | 2006-014928 A | 1/2006 |

* cited by examiner

*Primary Examiner* — Chuong A. Luu
(74) *Attorney, Agent, or Firm* — Birch, Stewart, Kolasch & Birch, LLP

(57) ABSTRACT

An image display device has a point setting section for setting a point for each of multiple medical images representing a subject; a size determining section that determines a common size that fits for each image shown at the point set by the point setting section in each of the multiple medical images such that each image can be displayed within a display area of the common size; and a displaying section that displays the image in the display area of the common size.

10 Claims, 9 Drawing Sheets

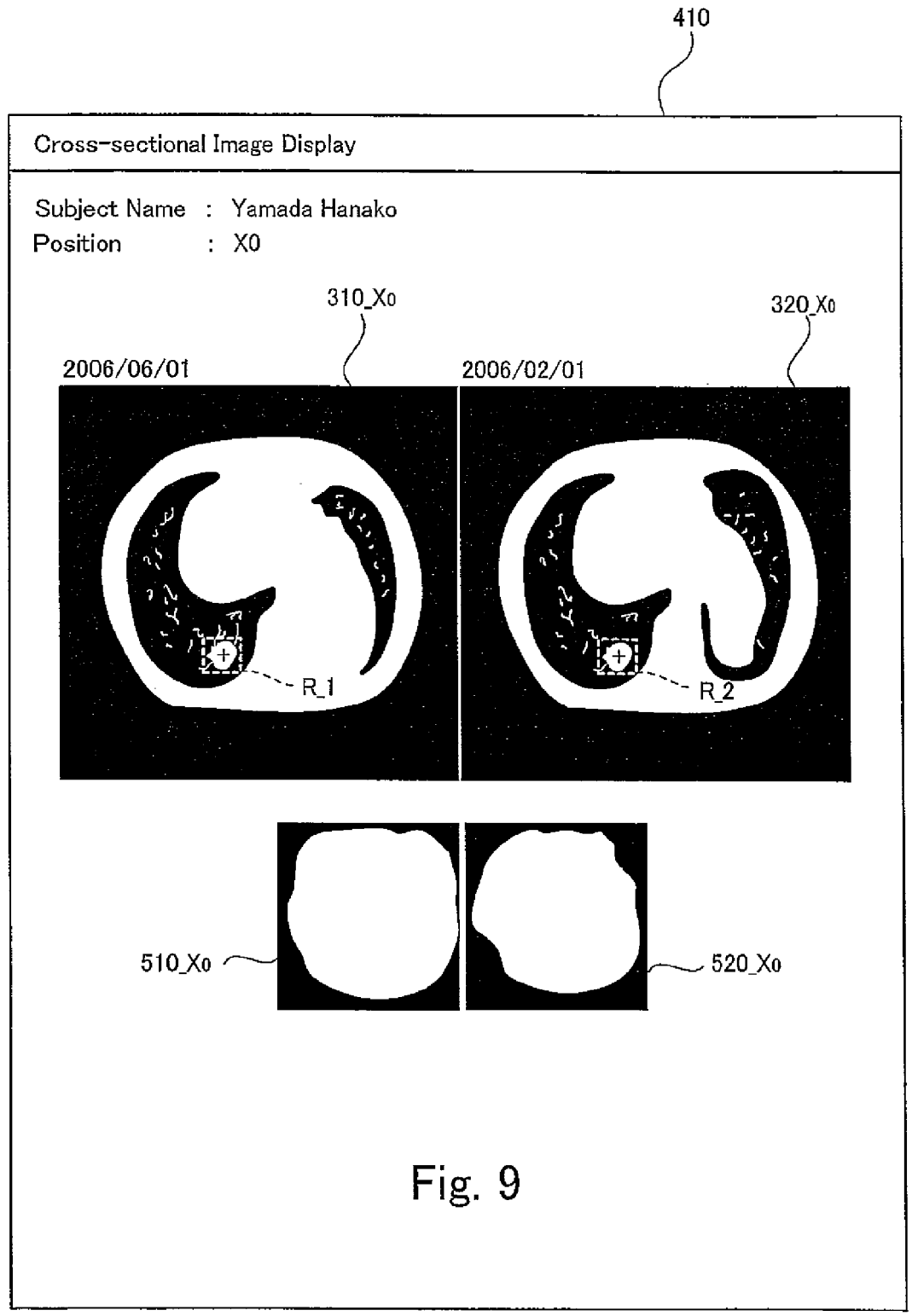

IMAGE DISPLAY DEVICE AND IMAGE DISPLAY PROGRAM STORAGE MEDIUM

BACKGROUND OF THE INVENTION

1. Field of the Invention

The present invention relates to an image display device and an image display program storage medium storing an image display program for displaying a medical image representing a photographed subject.

2. Description of the Related Art

In the medical field, it is widely practiced to utilize medical images representing a photographed internal body of a subject by using radiation or the like for the diagnosis of symptoms of the subject. Utilizing the medical images for the diagnosis enables a person in the medical field to grasp the stages of symptoms of the subject or the like without causing any outer damage to the subject and thus obtain necessary information to determine treatment plans or the like.

Further, in recent years, such devices as CR (Computed Radiography) for obtaining digitalized medical images by using radiation, CT (Computerized Tomography) for obtaining cross-sectional images of the subject by using radiography, and MRI (Magnetic Resonance Imaging) for obtaining cross-sectional images of the subject by using strong magnetic fields are becoming widely used, and digitalized medical images are becoming commonly used instead of medical images using conventional X-ray films or the like. With the digitalization of medical images, it is possible to collectively manage the medical images together with a digitalized medical record of the subject, and to share the medical image and record among multiple hospitals or the like via network. Thus, even though a clinic or a hospital where the subject gets treatment is changed, the medical images and the medical record showing the latest history of disease of the subject can be utilized.

Here, in general, the medical images photographed at the time of examination are usually stored along with the medical record or the like categorized by each subject, and at the time of actual diagnosis, interpretation of radiogram is performed by arranging multiple medical images photographed at different times on a monitor. This interpretation of radiogram enables easy confirmation of change in the size of lesion or the like and is one of very useful methods for diagnosing symptoms and the effect of medical treatments.

Additionally, a technique is described in Japanese Patent Application Publication No. 2006-014928, which displays multiple medical images arranged on the monitor and, if any attention point is specified on these medical images, clips an attention area in a certain size by centering around the attention point and magnifies it on the monitor. According to the technique described in this Japanese Patent Application Publication No. 2006-014928, when a point considered as lesion is specified, an image portion of the specified point is automatically magnified, which makes the comparison of size of the lesion easier.

However, with the technique described in the Japanese Patent Application Publication No. 2006-014928, there is a concern that, when large lesion extends beyond the attention area, the shape and size of the lesion becomes hard to be recognized. In cases like this, a user needs to reset each of the attention area manually, which takes a lot of labor and time.

SUMMARY OF THE INVENTION

The present invention has been made in view of the above circumstances and provides an image display device and an image display program storage medium storing an image display program capable of automatically clipping and displaying a lesion area considered as the focus of disease on medical images in a suitable size.

An image display device according to the present invention includes:

a point setting section that sets a point on an image for each of a plurality of medical images representing a photographed subject;

a size determining section that determines a common size that fits for each image shown at the point set by the point setting section on each of the plurality of medical images so that each image can be displayed within a display area of the common size; and a displaying section that displays the image in the display area of the common size.

According to the image display device in the present invention, when a point is set for each of the multiple medical images, a common size is determined, which is capable of displaying each image photographed at the point within the display area, and the image is displayed within the display area of the common size. With this, it is possible to save the labor for setting an area including the whole image of lesion or the like each by each on the multiple medical images, and to display the whole image easily within the display area fitted to its size.

Further, it is desirable that, in the image display device according to the present invention, the displaying section displays each image shown in each of the plurality of medical images in a plurality of display areas aligned with one another.

By displaying each image shown in the multiple medical images in order, the comparison of change in the size and shape of lesion becomes easier.

Likewise, it is desirable that, in the image display device according to the present invention, the point setting section sets a point on an image for a part of medical images among the plurality of medical images in response to an operation, and, for medical images other than the medical image on which the point has been set among the plurality of medical images, sets a point corresponding to the set point.

According to this favorable image display device in the present invention, it is possible to save the labor of setting a point of lesion or the like manually each by each for each of the multiple medical images.

Moreover, it is desirable that, in the image display device according to the present invention, the plurality of medical images represents an identical subject photographed at different times.

According to this favorable image display device, it is possible to recognize change in the size of lesion of the subject easily.

Also, it is desirable that, in the image display device according to the present invention, the plurality of medical images are cross-sectional images constituting a cross-sectional image group having a plurality of cross-sectional images at a plurality of cutting positions arranged in a predetermined direction in the subject, and the plurality of medical images are a plurality of cross-sectional images with a common cutting position, belonging to different cross-sectional image groups;

the size determining section determines the common size that fits for size of each image constituting a series of image group including an image shown at the position, the image appearing over a plurality of cross-sectional images in the cross-sectional image groups, such that each image constituting each of image groups belonging to the cross-sectional image groups different from each other can be displayed within a display area of the common size; and the displaying section displays an image constituting the image group in the display area of the common size, and displays another image belonging to the image group by switching from the displayed image in response to a predetermined operation.

By changing an image to display in the display area in response to an operation, the user can easily confirm the image at various cutting positions and recognize the shape and size of the lesion or the like in three dimensions. Furthermore, by determining a common size capable of displaying all images constituting a series of image groups over multiple cross-sectional images within the display area, it is possible to always display images useful for diagnosis without lacking the edge of lesion or the like at the time of switching images to be displayed in the display area.

Additionally, an image display program storage medium according to the present invention stores an image display program that is executed in a computer to build on the computer: a point setting section that sets a point on an image for each of a plurality of medical images representing a photographed subject;

a size determining section that determines a common size that fits for each image shown at the point set by the point setting section on each of the plurality of medical images so that each image can be displayed within a display area of the common size; and a displaying section that displays the image in the display area of the common size.

According to the image display program storage medium in the present invention, it is possible to build an image display device capable of displaying a whole image within the display area fitted to its size.

Please note that, for the image display program storage medium, only its basic embodiments are shown here. This is simply to avoid redundancy and in a size-measuring program according to the present invention, not only the basic embodiments, but also various kinds of embodiments corresponding to the image display device are included.

Moreover, such elements as the point setting section and others that the image display program storage medium in the present invention builds on the computer system may be in either way that one element is built by one program part or that multiple elements are built by one program part. In addition, these elements may be either built to execute such actions by themselves, built to give an execution order to other programs or program parts embedded in the computer system.

As described above, according to the present invention, a lesion area considered as the focus of disease can be clipped in a suitable size and enlarged for viewing.

BRIEF DESCRIPTION OF THE DRAWINGS

The embodiments of the present invention will be described below with reference to the accompanying drawings.

FIG. 9 is a diagram showing one example of the cross-sectional image display screen on which a clipped image is displayed.

DETAILED DESCRIPTION OF THE INVENTION

Figure 1:
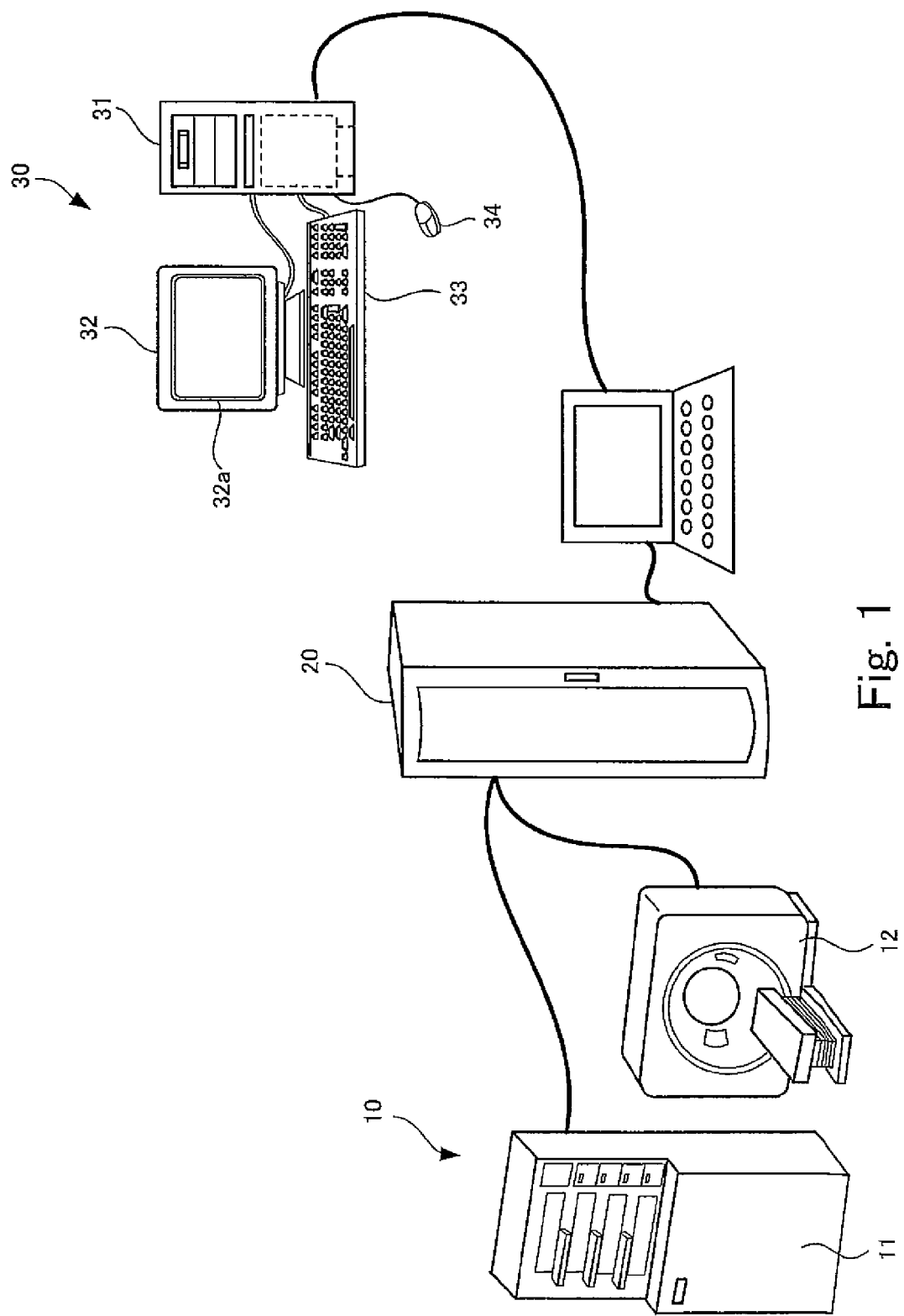
FIG. 1 is a diagrammatic sketch showing a configuration of a medical diagnosis system to which one embodiment of the present invention is applied.

FIG. 1 is a diagrammatic sketch showing a configuration of a medical diagnosis system to which one embodiment of the present invention is applied.

The medical diagnosis system shown in FIG. 1 has an image generation unit 10 for generating medical images by photographing internal body of a subject, a management server 20 for storing medical images and medical records, and a diagnosis unit 30 for displaying medical images. The image generation unit 10 and the management server 20 as well as the management server 20 and the diagnosis unit 30 are connected to each other via a network.

At this medical diagnosis system, an ID number for identifying the subject is assigned to each subject at the initial visit, and the ID number and its corresponding medical record showing the name, age, history of disease or the like are registered with the management server 20.

The image generation unit 10 includes a CR unit 11 for applying radiation to a subject and generating a digital medical image by reading the radiation passing through the subject, a MRI unit 12 for generating a cross-sectional image of the subject by using a strong magnetic field and radio waves, a CT unit (not shown) for generating a cross-sectional image of the subject by using radiation, and an ultrasonic unit (not shown) for generating a medical image by reading an ultrasonic echo. The medical images generated at the image generation unit 10 are transmitted to the management server 20 along with an ID number for identifying the subject of the medical images.

When the medical images and the ID number are transmitted from the image generation unit 10, the management server 20 stores the medical images by matching them with the ID number. That is, in the management server 20, the ID number, the medical record of the subject with the assigned ID number, and the matched medical images of the subject are registered.

The diagnosis unit 30 is equipped with as its external configuration, a main unit 31, an image display unit 32 for displaying an image on a display screen 32a in response to an instruction from the main unit 31, a keyboard 33 for inputting various kinds of information to the main unit 31 in response to the key operation, and a mouse 34 for inputting an instruction corresponding to, for example, an icon displayed at a position by specifying any position on the display screen 32a.

When a user inputs a name and an ID number of the subject by using the mouse 34 or the like of the diagnosis unit 30, the inputted content is conveyed to the management server 20. The management server 20 then transmits a medical image and a medical record matched with the name and the ID number of the subject that is conveyed from the diagnosis unit 30 to the diagnosis unit 30. The diagnosis unit 30 displays on the display screen 32a the medical image transmitted from the management server 20. By checking the medical image displayed on the display screen 32a of the diagnosis unit 30, the user can diagnose disease presentation of the subject without causing any outer damage to the subject.

The user diagnoses the disease presentation of the subject by watching the medical image displayed on the display screen 32a of the diagnosis unit 30, and edits the medical record by using the mouse 34 and the keyboard 33. The medical record after the edit is transmitted to the management server 20 and the medical record having been stored in the management server 20 is updated to a new medical record transmitted from the diagnosis unit 30.

The medical diagnosis system shown in FIG. 1 basically has the configuration described above.

Here, the feature as one embodiment of the present invention in the medical diagnosis system lies in the content of processing executed at the diagnosis unit 30. Hereinafter, a detailed explanation will be given about the diagnosis unit 30.

Figure 2:
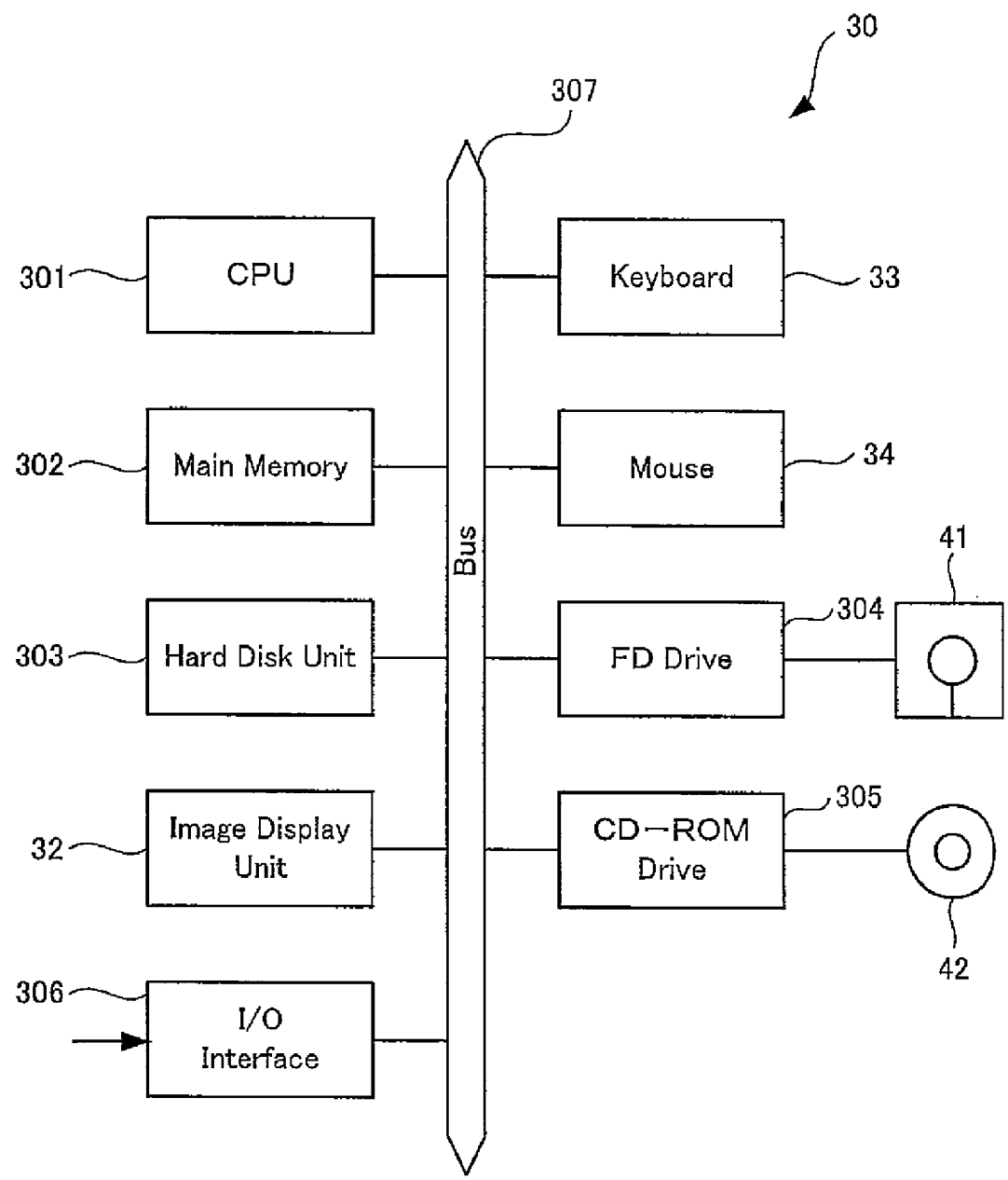
FIG. 2 is a hardware configuration of a medical diagnosis device.

FIG. 2 is a drawing of a hardware configuration of the diagnosis unit 30.

As shown in FIG. 2, the main unit 31 of the diagnosis unit 30 is internally equipped with a CPU 301 for executing various kinds of programs, a main memory 302 for reading a program stored in a hard disk unit 303 and expanding for the execution by the CPU 301, the hard disk unit 303 for storing various kinds of programs and data or the like, a FD drive 304 for accessing a FD 41 loaded therein, a CD-ROM drive 305 for accessing a CD-ROM 42 loaded therein, and an I/O interface 306 for receiving image date and so on from the management server 20 and transmitting various kinds of instructions to the management server 20. These various kinds of elements and furthermore, the image display unit 32, the keyboard 33, the mouse 34, which are also shown in FIG. 1, are connected to one another via a bus 307.

Here, the CD-ROM 42 stores a medical image display program 100 (See FIG. 3), which is one embodiment of the image display program storage medium in the present invention, for constructing in the diagnosis unit 30 one embodiment of the image display unit in the present invention.

Figure 3:
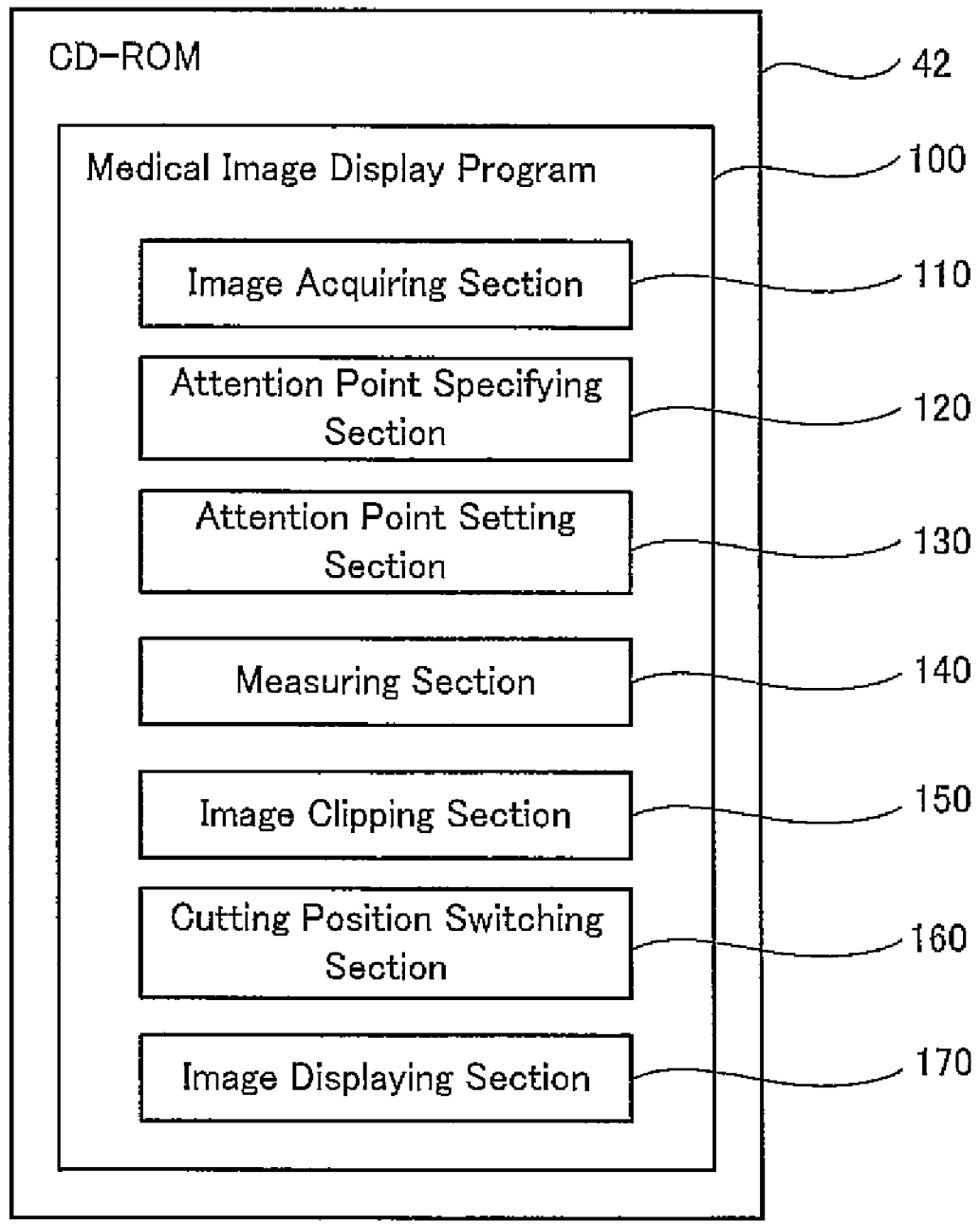
FIG. 3 is a conceptual illustration of a CD-ROM.

FIG. 3 is a conceptual illustration showing the CD-ROM 42.

As shown in FIG. 3, the medical image display program 100 stored in the CD-ROM 42 is constituted of an image acquiring section 110, an attention point specifying section 120, an attention point setting section 130, a measuring section 140, an image clipping section 150, a cutting position switching section 160, and an image displaying section 170.

The CD-ROM 42 is inserted into the CD-ROM drive 305 of the diagnosis unit 30, and the medical image display program 100 stored in the CD-ROM 42 is uploaded to the diagnosis unit 30 and stored in the hard disk unit 303. Launching and executing this medical image display program 100 constructs in the diagnosis unit 30 a medical image display unit 200 (See FIG. 4) as one embodiment of the medical image display device in the present invention.

Additionally, although in the above-description, the CD-ROM 42 exemplifies a storage medium for storing the medical image display program 100, the storage medium for storing the medical image display program 100 is not limited to a CD-ROM, but also it may be any other storage media such as an optical disk, an MO, an FD, and a magnetic tape. Furthermore, the medical image display program 100 may be directly supplied to the diagnosis unit 30 via the I/O interface 306 without going through any storage media.

Details of each section of the medical image display program 100 will be explained along with the action of each section of the medical image display unit 200.

Figure 4:
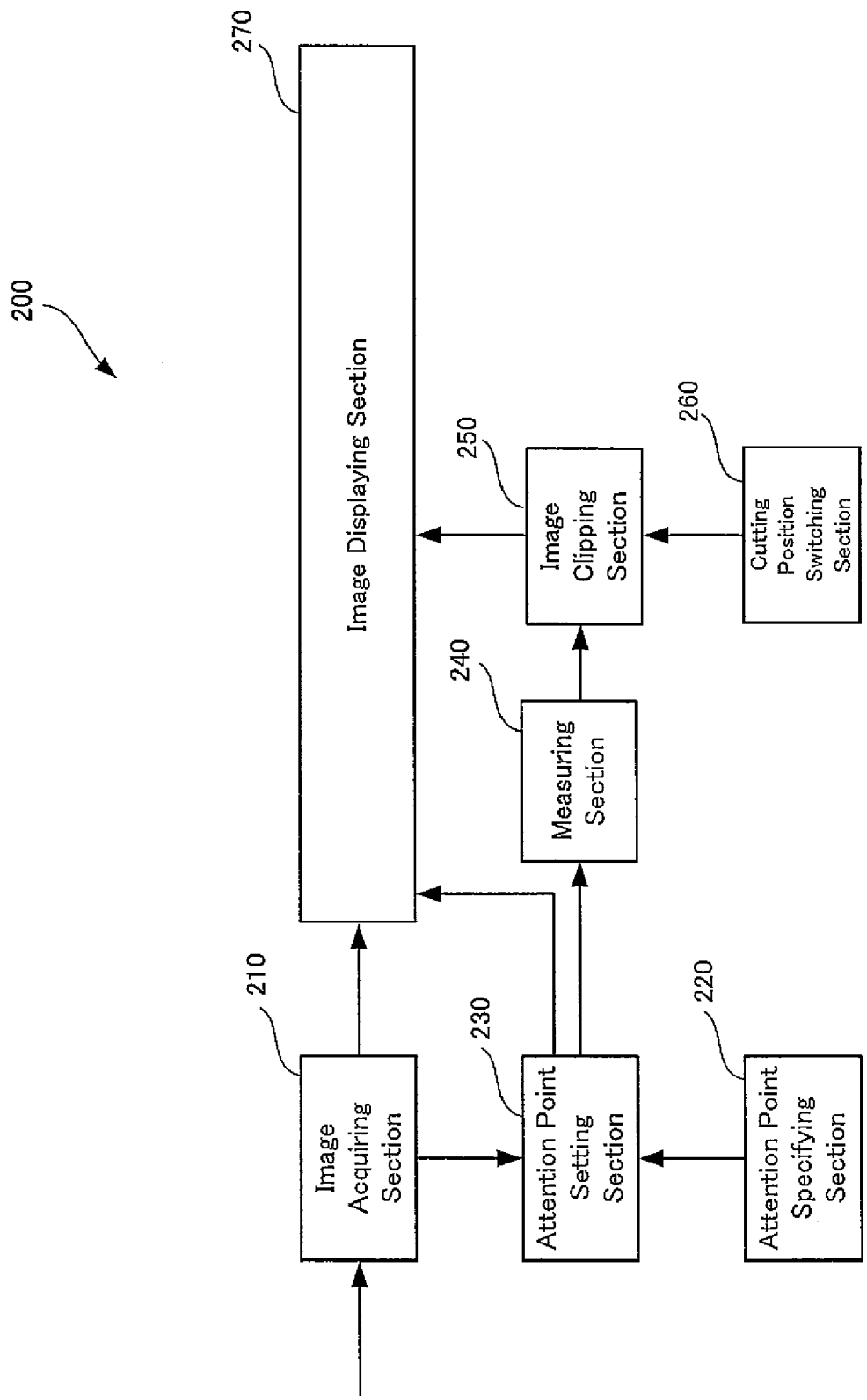
FIG. 4 is a functional block diagram of a medical image display unit.

FIG. 4 is a functional block diagram of the medical image display unit 200.

The medical image display unit 200 has an image acquiring section 210, an attention point specifying section 220, an attention point setting section 230, a measuring section 240, an image clipping section 250, and an image displaying section 270.

The image acquiring section 210, the attention point specifying section 220, the attention point setting section 230, the measuring section 240, the image clipping section 250, the cutting position switching section 260, and the image displaying section 270, which constitute the medical image display unit 200 correspond to the image acquiring section 110, the attention point specifying section 120, the attention point setting section 130, the measuring section 140, the image clipping section 150, the cutting position switching section 160, and the image displaying section 170, respectively.

Each element in FIG. 4 differs from each element in FIG. 3 on the point that each element in FIG. 4 is constituted of the combination of computer hardware, OS and an application program executed in the computer, while each element of the medical image display program 100 shown in FIG. 3 is constituted of the application program only.

Figure 5:
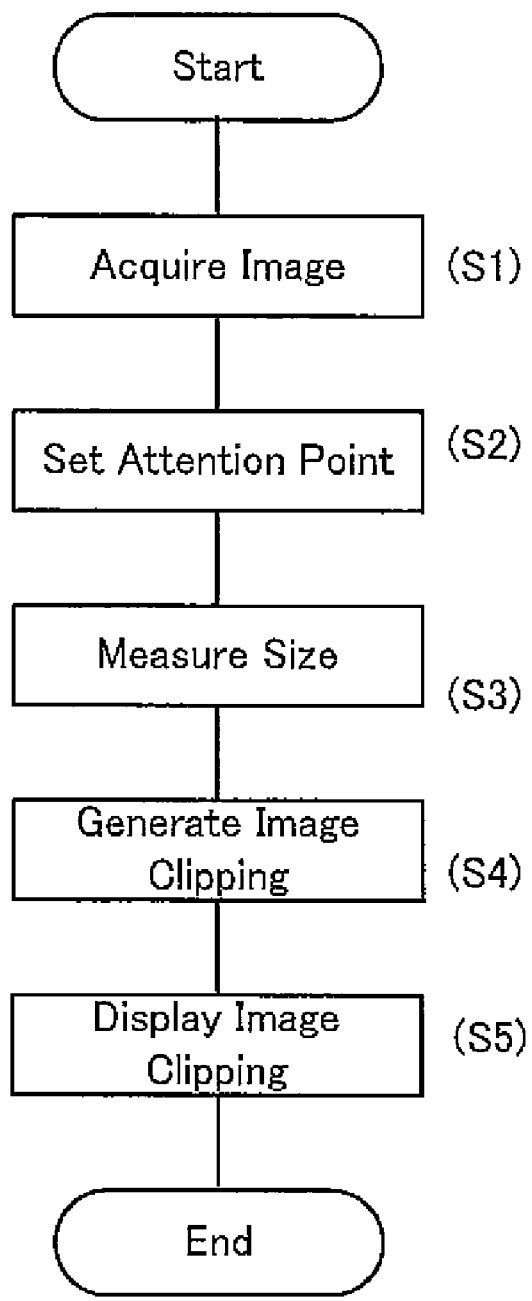
FIG. 5 is a flowchart illustrating a series of processing that starts from acquiring a medical image from a management server to end by displaying the acquired medical image.

FIG. 5 is a flowchart showing a series of processing flow in the medical image display unit 200 shown in FIG. 4, from when a medical image is acquired from the management server 20 until when the acquired medical image is displayed.

Hereinafter, following the flowchart in FIG. 5, an explanation will be given about the action of each element of the medical image display unit 200 shown in FIG. 4, which also explains each element of the medical image display program 100 shown in FIG. 3.

When the user inputs a name and an ID number of the subject for diagnosis by using the mouse 34 and the keyboard 33 shown in FIG. 1, the inputted content is conveyed to the management server 20 via the I/O interface 306 in FIG. 2. From the management server 20, a medical image and a medical record matched with the name and ID number having been conveyed from the diagnosis unit 30 are transmitted toward the diagnosis unit 30.

The medical image transmitted from the management server 20 is acquired at the image acquiring section 210 shown in FIG. 4 (step S1 in FIG. 5).

Figure 6:
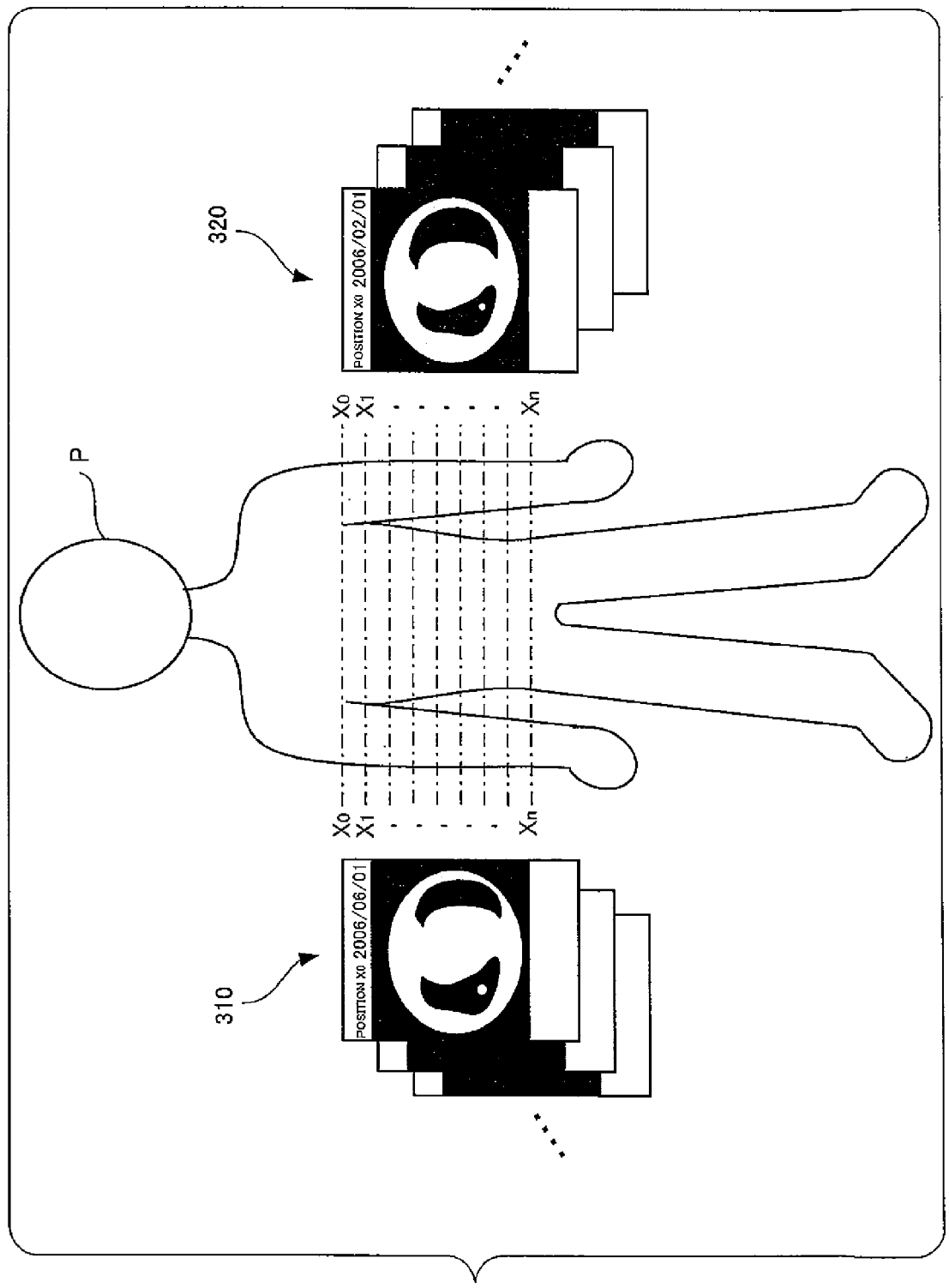
FIG. 6 is a diagram showing an image of a medical image transmitted from the management server.

FIG. 6 is a drawing showing an image of the medical image transmitted from the management server 20.

At the MRI unit 12 shown in FIG. 1, in a state where a subject P lies down with the head positioned at a predetermined location on an inspection table, each cross-section is photographed by cutting at predetermined intervals (slice width) within a photographing area that includes from the chest to the base of the ankle of the subject P. In this example, the same subject P is photographed twice by using the MRI unit 12 with the setting of the same slice width at different times to each other, and in each photographing, cross-sectional image groups 310, 320 constituted of multiple cross-sectional images are generated and stored in the management server 20. In this example, since the cross-sectional image groups 310, 320 are photographed with the setting of the same slice width, the cross-sectional images of the same slice number indicate that the same cutting position within the photographing area has been photographed. Therefore, the explanation will be given by representing a cutting position of the slice number i as Xi, and cross-sectional images at the cutting position Xi as 310_Xi, 320_Xi. At the image acquiring section 210, these cross-sectional image groups 310, 320 in two times are acquired, and then the acquired cross-sectional image groups 310, 320 are conveyed to the image displaying section 270 and the attention point setting section 230.

The image displaying section 270 displays a cross-sectional image display screen 410 (See FIG. 7) including the cross-sectional image groups 310, 320 conveyed from the image acquiring section 210 on the display screen 32a shown in FIG. 1. The image displaying section 270 corresponds to one example of the displaying section according to the present invention.

Figure 7:
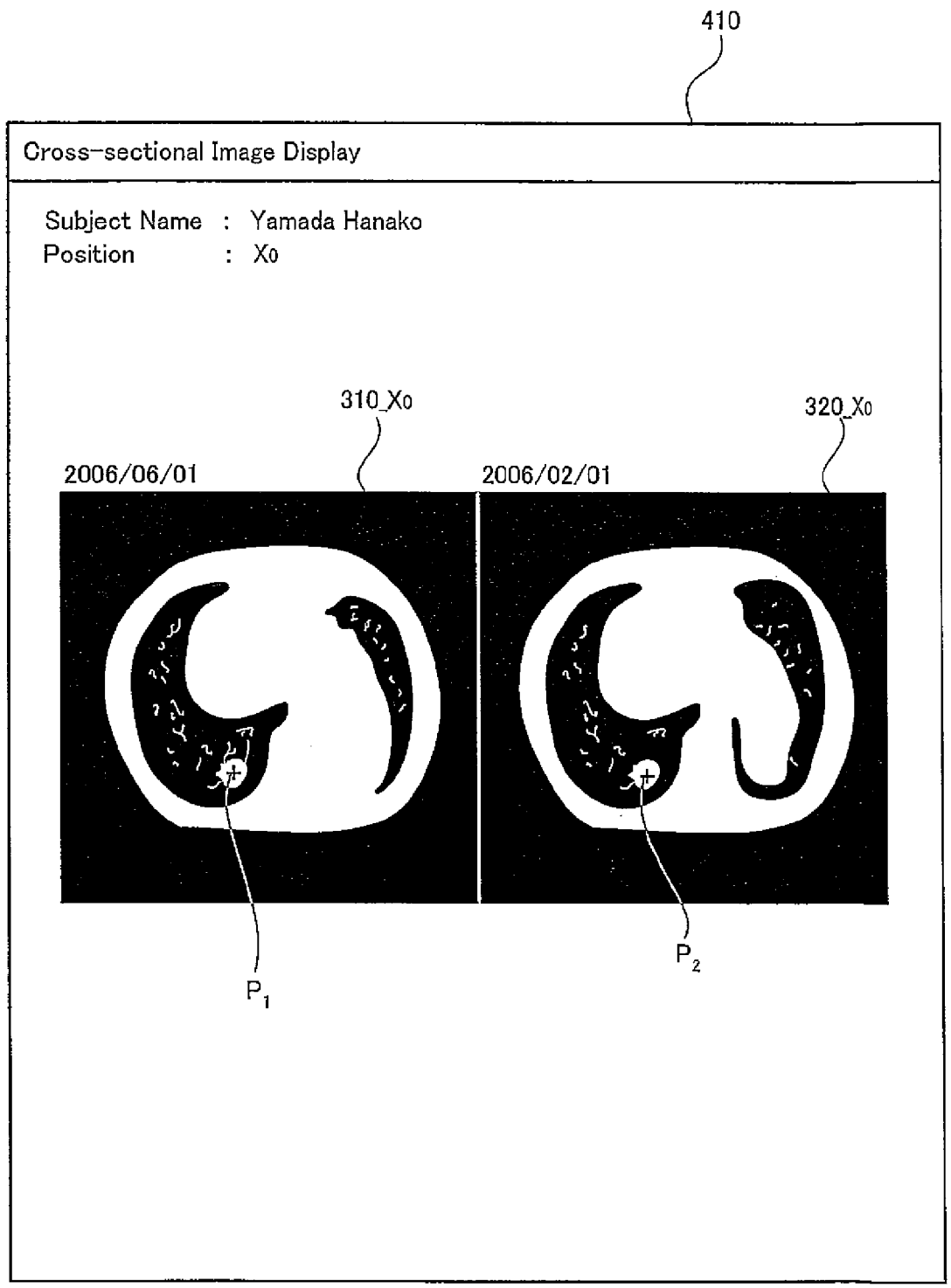
FIG. 7 is a diagram showing one example of a cross-sectional image display screen.

FIG. 7 is a drawing showing one example of the cross-sectional image display screen.

On the cross-sectional image display screen 410 shown in FIG. 7, the cross-sectional images 310_X0, 320_X0 at a cutting position X0 corresponding to the edge of the photographing area are displayed among the cross-sectional images constituting the cross-sectional image groups 310, 320. And further, the cutting position of these cross-sectional images 310_X0, 320_X0, photographing date, and subject name and so on are displayed.

These two cross-sectional images 310_X0, 320_X0 are images in which cross-sections at the same cutting position of the same subject are photographed respectively at different times, and by comparing these, change in the focus of disease or the like can be confirmed. However in a case where the change in the focus of disease is small, there is a problem that the change is hard to be recognized only through the comparison of these images.

At the medical image display unit 200 in the present embodiment, first of all, an attention point P1 is set on either one of the cross-sectional images out of the two cross-sectional images 310_X0, 320_X0 (step S2 in FIG. 5). In the example of FIG. 7, when the user clicks any attention point on the cross-sectional image 310_X0 on the left side with the use of the mouse 34 shown in FIG. 1, the position of the clicked attention point is conveyed from the attention point specifying section 220 to the attention point setting section 230 shown in FIG. 4.

The attention point setting section 230 determines the specified attention point as the attention point P1 for the cross-sectional image on which the attention point has been specified out of the cross-sectional images 310_X0, 320_X0, and for the cross-sectional image on which the attention point has not been specified, the same point as the attention point having been determined for the other cross-sectional image is determined as an attention point P2. In the example of FIG. 7, by clicking a lesion point on the cross-sectional image 310_X0 on the left side, the lesion point is determined as the attention point P1, and a point corresponding to the attention point P1 on the cross-sectional image 320_X0 on the right side is determined as the attention point P2. Further, on the multiple cross-sectional images constituting the cross-sectional image group 310, the same position as the attention point P1 is determined as the attention point P1, and on the multiple cross-sectional images constituting the cross-sectional image group 320, the same position as the attention point P2 is determined as the attention point P2. The attention point specifying section 220 combined with the attention point setting section 230 correspond to one example of the point setting section according to the present invention. The position of the determined attention points P1, P2, and the cross-sectional image groups 310, 320 are conveyed to the measuring section 240.

At the measuring section 240, lesion images S1, S2 including the attention points P1, P2 on the cross-sectional images 310_X0, 320_X0 are extracted, and the major axis and minor axis of these lesion images S1, S2 (see FIG. 8) are measured for each (step S3 in FIG. 5).

A simple explanation will be given about the method for extracting and measuring the lesion images S1, S2 including the attention points P1, P2.

Recently, machine learning has been widely utilized, which calculates characteristic amount of image of many varied types such as the maximum value, minimum value, average value, and median value of pixels for each of the multiple sample images photographed in various scenes and makes the computer learn to associate each scene with its characteristic amount. The use of this machine learning enables handling of a large amount of characteristic that a human cannot handle as well as findings of correlation that is impossible to think of with the imagination of a human, and is known to realize judgment with great precision. The measuring section 240 in the present embodiment stores beforehand image characteristics in standard lesion images previously known as tumor or the like in cross-sectional images and the lesion images are searched by utilizing the machine learning.

At the measuring section 240, first of all, attention areas R1, R2 surrounding the attention points P1, P2 in each of cross-sectional images 310_X0, 320_X0 are determined. The size of these attention areas R1, R2 has been prepared beforehand as an empirical value in which a general tumor or the like can be surely included.

Next, image characteristics of each pixel included in each attention area R1, R2 are analyzed, and pixels that match the image characteristics of lesion portion having been previously stored are searched out of the pixels in each attention area R1, R2.

Further, for the pixels having matched the features of the lesion portion, evaluation is conducted whether each pixel is the pixel constituting the outline of lesion image, and the outline of the lesion images S1, S2 which includes the attention points P1, P2 and can be predicted as the lesion portion is extracted out of the attention areas R1, R2.

When the outline of the lesion images S1, S2 is extracted, the major axis and minor axis of each of lesion images 1, S2 are measured.

The series of processing that extracts, upon the specification of the attention points P1, P2, the outline of the lesion images S1, S2 including the attention points and further measures the major axis and minor axis of each lesion image S1, 32 is a technique devised as one click measurement.

At the measuring section 240, in the same manner as the cross-sectional images 310_X0, 320_X0, also for other cross-sectional images constituting each of the cross-sectional image groups 310, 320, the major axis and minor axis of the lesion image are measured respectively. The lesion images S1, 32 having been extracted in the process of measuring the major axis and minor axis are conveyed to the image clipping section 250 along with the cross-sectional image groups 310, 320.

At the image clipping section 250, among the cross-sectional images 310_X0, 320_X0, a clipped image is generated, by cutting an image portion including the whole extracted lesion images S1, S2 (step S4 in FIG. 5).

Figure 8:
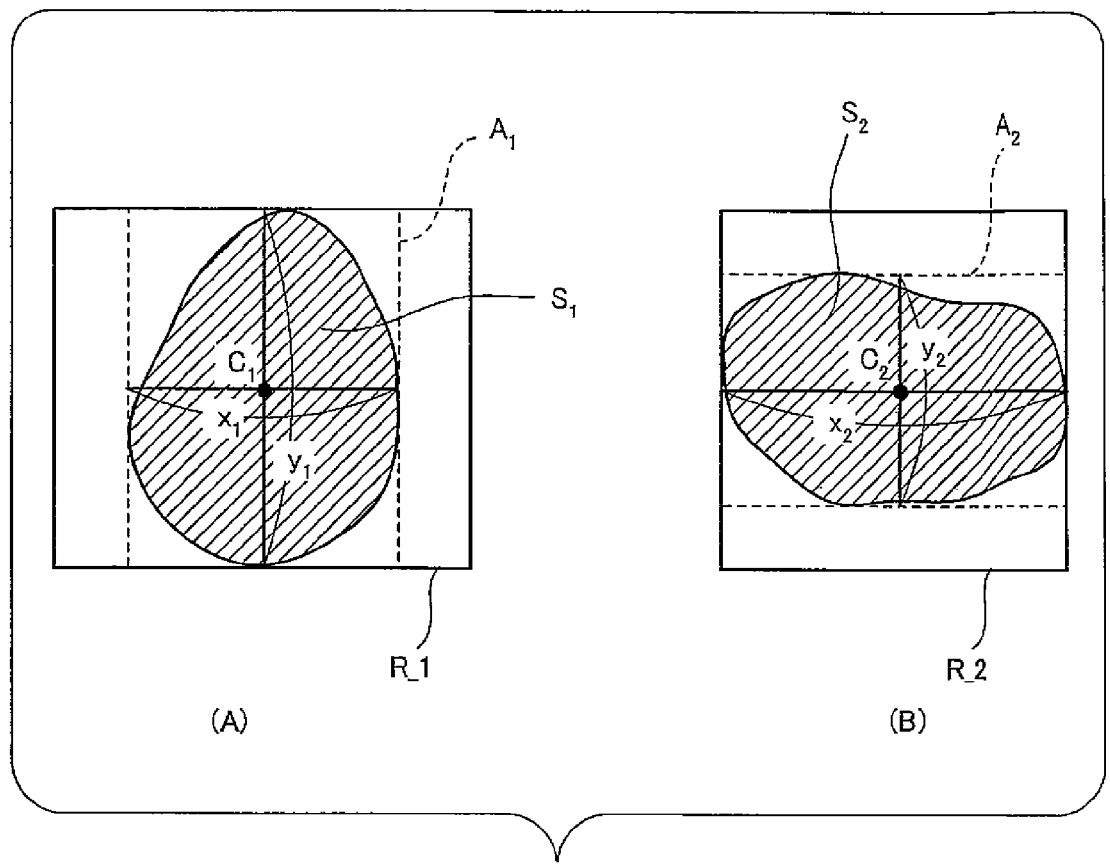
FIG. 8 is a conceptual illustration of a method for generating a clipped image.

FIG. 8 is a conceptual image showing a method for generating a clipped image.

At the image clipping section 250, first of all, minimum inclusive rectangles A1, A2 inclusive each of lesion images S1, S2 are calculated.

Then, center points C1, C2 of the calculated minimum inclusive rectangles A1, A2, length in the horizontal direction x1, x2 and length in the vertical direction y1, y2 of the minimum inclusive rectangles A1, A2 are calculated respectively.

When each center point and size of the minimum inclusive rectangles A1, A2 has been calculated, then an image portion including the attention points P1, P2 is cut out from the cross-sectional images 310_X0, 320_X0. If the length that is the longer of the two between the length x1, x2 in the horizontal direction of each minimum inclusive rectangles A1, A2 is specified as Lx (Lx=x2 in FIG. 8), the length that is the longer of the two between the length y1, y2 in the vertical direction of each minimum inclusive rectangles A1, A2 is specified as Ly (Ly=y1 in FIG. 8), and a predetermined extra width is specified as h (for example, about 5 pixels), then an image portion contained in a rectangle of which size is within the horizontal length of (Lx+h) and the vertical length of (Ly+h), having the central points C1, C2 is cut out from the cross-sectional images 310_X0, 320_X0, and thus the clipped images 510_X0, 520_X0 are generated. The combination of the measuring section 240 and the image clipping section 250 correspond to one example of the size determining section according to the present invention.

The generated clipped images 510_X0, 520_X0 are conveyed to the image displaying section 270.

The image displaying section 270 displays the clipped images 510_X0, 520_X0 conveyed from the image clipping section 250 in a clipped image display area of which size has been predetermined, on the cross-sectional image display screen 410 shown in FIG. 7 by enlarging the clipped images to become the same size as the image clipping display area.

FIG. 9 is a drawing showing one example of the cross-sectional image display screen 410 on which the clipped images 510_X0, 520_X0 are displayed.

On the cross-sectional image display screen 410 shown in FIG. 9, enlarged view of the clipped images 510_X0, 520_X0 generated at the image clipping section 250 are arranged, and on the cross-sectional images 310_X0, 320_X0, a frame is shown for the clipping areas R_1, R_2 from which the clipped images 510_X0, 520_X0 have been clipped.

In this way, according to the present embodiment, the user only needs to specify an attention point considered as the focus of disease on one cross-sectional image 310_X0 to set the same position as the specified position on the other cross-sectional image 320_X0 as the attention point, and the whole lesion image including the attention point in each of the cross-sectional images 310_X0, 320_X0 are clipped in the size proportional to the size of the lesion image and enlarged for display. Because of this, even in a case where examination results in multiple times are compared at one time, useful images for diagnosis can be obtained easily, while at the same time omitting the labor and time for setting attention area each by each on many medical images.

Also, in a state shown in FIG. 9, if the user turns the wheel of the mouse 34, an instruction to switch cutting position is issued from the cutting position switching section 260 to the image clipping section 250 shown in FIG. 4.

At the image clipping section 250, clipped images 510_Xn, 520_Xn are generated from the cross-sectional images 310_Xn, 320_Xn at a cutting position Xn that is away from each cutting position X0 of the currently displayed cross-sectional images 310_X0, 320_X0 in the direction of wheel rotation for the distance proportional to the rotating amount of the wheel. And the generated clipped images 510_Xn, 520_Xn and the cross-sectional images 310_Xn, 320_Xn are conveyed to the image displaying section 270 as well. At the image displaying section 270, the cross-sectional images 310_Xn, 320_Xn and the clipped images 510_Xn, 520_Xn are displayed on the cross-sectional image display screen 410. The user can give an instruction to switch cutting positions for viewing so that the focus of disease can be checked at various cutting positions, and thus the shape and size or the like of the focus of disease can be grasped in three-dimensions.

As described above, according to the present embodiment, it is possible to easily enlarge the lesion portion in the medical image considered as the focus of disease, for viewing without lacking its outer edge or the like.

Now that the explanation of the first embodiment in the present invention is finished, an explanation will be given about a second embodiment of the present invention. Since the second embodiment in the present invention has a configuration similar to the first embodiment shown in FIG. 4, so that FIGS. 4, 8 are also used for the explanation of the second embodiment, and only different points from the first embodiment will be explained.

At the measuring section 240 in the present embodiment, by executing the three-dimensional one click measurement, firstly, three-dimensional attention areas R1, R2 are determined, which surround the whole attention points P1, P2 set for each of the multiple cross-sectional images arranged in the direction of Z-axis of the cross-sectional image groups 310, 320, respectively. The size of these attention areas R1, R2 has also been prepared beforehand as empirical value in which general tumors or the like are certainly included.

Next, for each cross-sectional image included in the attention areas R1, R2, by extracting the lesion images S1, S2 including the attention points P1, P2, lesion image groups S1', S2' are extracted, in which the lesion images S1, S2 are piled in the direction of Z-axis, on the multiple cross-sectional images included in each attention area R1, R2.

At the image clipping section 250, a common size for the clipping area including any one of the multiple lesion images S1, S2 constituting each lesion image group S1', S2' is calculated, and a clipped image is generated, which is a clipping of the lesion images S1, S2 in the clipping area.

Here, Parts (A) and (B) of FIG. 8 will be explained as a drawing showing a three-dimensional area.

At the image clipping section 250, first of all, minimum inclusive rectangular solids A1, A2 including the whole three-dimensional lesion image groups S1', S2' are calculated.

Then, on the cross-sectional image included in the minimum inclusive rectangular solids A1, A2, the center points C1, C2 of the rectangular area corresponding to the cross-section of the calculated minimum inclusive rectangular solids A1, A2 as well as the length x1, x2 in the direction of X-axis, and the length of y1, y2 in the direction of Y-axis of the minimum inclusive rectangular solids A1, A2 are calculated.

If the length that is the longer of the two between the length x1, x2 in the horizontal direction of the minimum inclusive rectangles A1, A2 is specified as Lx (Lx=x2 in FIG. 8), the length that is the longer of the two between the length y1, y2 of each vertical direction of the minimum inclusive rectangles A1, A2 is specified as Ly (Ly=y1 in FIG. 8), and a predetermined extra width is specified as h (for example, about 5 pixels), then a rectangular area having the horizontal length of (Lx+h) and the vertical length of (Ly+h), with the central points C1, C2 is cut out on each of cross-sectional images constituting the cross-sectional image groups 310_X0, 320_X0, and thus the clipped image groups 510, 520 are generated.

The generated clipped image groups 510, 520 are conveyed to the image displaying section 270.

The image displaying section 270 displays enlarged view of the clipped images 510_X0, 520_X0 corresponding to the cutting position X0 currently displayed, among the clipped image groups 510, 520 conveyed from the image clipping section 250, which are arranged in order in the close proximity of the cross-sectional images 310_X0, 320_X0 on the cross-sectional image display screen 410 shown in FIG. 7.

When the user turns the wheel of the mouse 34, the cross-sectional images 310_Xn, 320_Xn and the clipped images 510_Xn, 520_Xn at the cutting position of Xn that is away from the present cutting position X0 for a distance proportional to the rotating amount of the wheel are displayed on the cross-sectional image display screen 410.

In this way, by utilizing the three-dimensional one click measurement, the three-dimensional lesion image groups S1', S2' are extracted, and a common size is determined for the clipping area in which any of the multiple lesion images S1, S2 constituting each of lesion image groups S1', S2' are included. By generating the clipped images of the common size, clipped images useful for diagnosis without lacking the edge of lesion portion can be swiftly and surely displayed even if the cutting position is switched.

Here, although in the above-description, the explanation has been made about the example of displaying the cross-sectional images included in two sets of cross-sectional image groups, the image displaying section according to the present invention may display the cross-sectional images included in not less than three sets of cross-sectional image groups.

Further, although in the above-description, the explanation has been made about the example of specifying the attention point on the cross-sectional images, the point setting section according to the present invention may specify an attention area in cross-sectional images.

Furthermore, although in the above-description, the explanation has been made about the example of manually specifying the attention point the user guesses as the focus of disease on the cross-sectional image, the point setting section according to the present invention may search, for example, an image portion having an image pattern similar to a sample image in the cross-sectional images by image processing, and set the searched image portion as the attention point.

Moreover, the image display device according to the present invention may store the position of a lesion portion on the cross-sectional images photographed in the past, and when a new set of the cross-sectional images can be obtained, display a list of the past lesion portion, acquire the position of the lesion portion selected by the user, and set as the attention point this time.

Also, the image display device according to the present invention may set, for example, a central point of the right lung field or left lung field as an attention point when the attention point on the right lung field or the left lung field is specified.

Additionally, although in the above-description, the explanation has been made about the example of applying the image display device according to the present invention for the diagnosis unit, the image display device according to the present invention may be applied to the management server or the like.

What is claimed is:

1. An image display device comprising:
  a point setting section that sets, in response to an operation, a point on one medical image among a plurality of medical images representing cross-sections at the same cutting position of an identical subject photographed at different times, and sets a point on each of medical images other than the one medical image, on which the point has been set, among the plurality of medical images, the point on the each of the medical images other than the one medical image corresponding to the set point on the one medical image;
  a size determining section that determines a common size by obtaining the minimum value of a respective size of regions that are able to include each extracted image extracted based on the point set by the point setting section on each of the plurality of medical images and obtaining the common size based on the minimum value of sizes of each region so that the each extracted image can be displayed within a display area of the common size; and
  a displaying section that displays the extracted image in the display area of the common size.

2. The image display device according to claim 1, wherein the plurality of medical images are cross-sectional images each belonging to a cross-sectional image group having one or more cross-sectional images at one or more cutting positions arranged in a predetermined direction in the subject, and the plurality of medical images are a plurality of cross-sectional images with a common cutting position, belonging to different cross-sectional image groups;
  the size determining section determines the common size that fits for size of each of extracted images constituting a series of extracted image groups each of which includes one of the plurality of extracted images extracted from the point on the plurality of medical images, the each of, the series of extracted image groups ranging over the one or more cross-sectional images in one of the different cross-sectional image groups, so that the each of the extracted images constituting the series of extracted image groups in the different cross-sectional image groups can be displayed within a display area of the common size; and
  the displaying section displays the each of the extracted images constituting the series of extracted image groups, and switches, in response to a predetermined operation, the displayed image from the each of the extracted images constituting the series of extracted image groups to another extracted image in a same extracted image group to which the each of the extracted images constituting the series of extracted image groups belongs.

3. The image display device according to claim 1, wherein the displaying section enlarges or reduces size of the extracted image so that the enlarged or reduced extracted image can be displayed within the display area of the common size.

4. A non-transitory computer-readable medium storing an image display program that is executed in a computer and causes the computer to operate as an image display device, the image display device comprising:
  a point setting section that sets, in response to an operation, a point on one medical image among a plurality of medical images representing cross-sections at the same cutting position of an identical subject photographed at different times, and sets a point on each of medical images other than the one medical image, on which the point has been set, among the plurality of medical images, the point on the each of the medical images other than the one medical image corresponding to the set point on the one medical image;
  a size determining section that determines a common size by obtaining the minimum value of a respective size of regions that are able to include each extracted image extracted based on the point set by the point setting section on each of the plurality of medical images and obtaining the common size based on the minimum value of sizes of each region so that the each extracted image can be displayed within a display area of the common size; and a displaying section that displays the extracted image in the display area of the common size.

5. An image display method comprising:

setting in response to an operation, a point on one medical image among a plurality of medical images representing cross-sections at the same cutting position of an identical subject photographed at different times, and setting a point on each of medical images other than the one medical image, on which the point has been set, among the plurality of medical images, the point on the each of the medical images other than the one medical image corresponding to the set point on the one medical image;

determining a common size by obtaining the minimum value of a respective size of regions that are able to include each extracted image based on the point set by the setting on each of the plurality of medical images and obtaining the common size based on the minimum value of sizes of each region so that each extracted image can be displayed within a display area of the common size; and displaying the extracted image in the display area of the common size.

6. An image display device comprising:

a point setting section that sets a point on each of a plurality of cross-sectional images each belonging to a cross-sectional image group having one or more cross-sectional images at one or more cutting positions arranged in a predetermined direction in a subject, the plurality of cross-sectional images being a plurality of cross-sectional images with a common cutting position and belonging to different cross-sectional image groups, a size determining section that determines a common size by obtaining the minimum value of a respective size of regions that are able to include each of extracted images constituting a series of extracted image groups each of which includes one of a plurality of extracted images extracted based on the points on the plurality of cross-sectional images, the each of the series of extracted image groups ranging over the one or more cross-sectional images in one of the different cross-sectional image groups and obtaining the common size based on the minimum value of sizes of each region, so that the each of the extracted images constituting the series of extracted image groups in the different cross-sectional image groups can be displayed within a display area of the common size; and a displaying section that displays the each of the extracted images constituting the series of extracted image groups in the display area of the common size.

7. The image display device according to claim 6, wherein the point setting section searches for a point where an image similar to a sample image appears in the cross-sectional image, and sets the point found by searching, in the cross-sectional image.

8. The image display device according to claim 6, further comprising:

a storage section that stores a point that has been set by the point setting section; and a past point display section that displays the point stored in the storage section, wherein the point setting section sets, in the cross-sectional image, a point selected from among points displayed by the past point display section.

9. An image display method comprising:

setting a point on each of a plurality of cross-sectional images each belonging to a cross-sectional image group having one or more cross-sectional images at one or more cutting positions arranged in a predetermined direction in a subject, the plurality of cross-sectional images being a plurality of cross-sectional images with a common cutting position and belonging to different cross-sectional image groups, a determining a common size by obtaining the minimum value of a respective size of regions that are able to include each of extracted images constituting a series of extracted image groups each of which includes one of a plurality of extracted images extracted based on the points on the plurality of cross-sectional images, the each of the series of extracted image groups ranging over the one or more cross-sectional images in one of the different cross-sectional image groups and obtaining the common size based on the minimum value of sizes of each region, so that the each of the extracted images constituting the series of extracted image groups in the different cross-sectional image groups can be displayed within a display area of the common size; and a displaying the each of the extracted images constituting the series of extracted image groups in the display area of the common size.

10. A non-transitory computer-readable medium storing an image display program that is executed in a computer causes the computer to operate as an image display device, the image display device comprising:

a point setting section that sets a point on each of a plurality of cross-sectional images each belonging to a cross-sectional image group having one or more cross-sectional images at one or more cutting positions arranged in a predetermined direction in a subject, the plurality of cross-sectional images being a plurality of cross-sectional images with a common cutting position and belonging to different cross-sectional image groups, a size determining section that determines a common size by obtaining the minimum value of a respective size of regions that are able to include each of extracted images constituting a series of extracted image groups each of which includes one of a plurality of extracted images extracted based on the points on the plurality of cross-sectional images, the each of the series of extracted image groups ranging over the one or more cross-sectional images in one of the different cross-sectional image groups and obtaining the common size based on the minimum value of sizes of each region, so that the each of the extracted images constituting the series of extracted image groups in the different cross-sectional image groups can be displayed within a display area of the common size; and a displaying section that displays the each of the extracted images constituting the series of extracted image groups in the display area of the common size.

* * * * *